United States Patent [19]
Vyas

[11] Patent Number: 6,111,101
[45] Date of Patent: Aug. 29, 2000

[54] PROCESS FOR THE PREPARATION OF 3,5-DIAMINO-6-(2,3-DICHLOROPHENYL)-1,2,4-TRIAZINE

[75] Inventor: Sharad Kumar Vyas, Gujarat State, India

[73] Assignee: Torrent Pharmaceuticals Ltd., Gujarat, India

[21] Appl. No.: 09/456,501

[22] Filed: Dec. 8, 1999

[30] Foreign Application Priority Data

Dec. 14, 1998 [IN] India ................. 2171/Cal/98

[51] Int. Cl.⁷ .................................... C07D 253/075
[52] U.S. Cl. ............................................ 544/182
[58] Field of Search ............................... 544/182

[56] References Cited

U.S. PATENT DOCUMENTS 4,602,017  7/1986  Sawyer et al. ................... 514/212

FOREIGN PATENT DOCUMENTS 0 247 892  5/1987  European Pat. Off. .
2 741 879  6/1997  France .
27 08 183  8/1978  Germany .

OTHER PUBLICATIONS

International Search Report for PCT/IB 99/01955.

*Primary Examiner*—John M. Ford
*Attorney, Agent, or Firm*—Sughrue, Mion, Zinn, Macpeak & Seas, PLLC

[57] ABSTRACT

There is disclosed an improved process for the preparation of 3,5-diamino-6-(2,3-dichlorophenyl)-1,2,4-triazine which process comprises the step of reacting 2,3-dichlorobenzoylchloride with cuprous cyanide in presence of acetonitrile and a cosolvent to produce dichlorobenzoyl cyanide, said dichlorobenzoyl cyanide is reacted with aminoguanidine bicarbonate to produce an intermediate product, which is cyclized in presence of aqueous potassium hydroxide to produce 3,5-diamino-6-(2,3-dichlorophenyl)-1,2,4-triazine.

11 Claims, No Drawings

PROCESS FOR THE PREPARATION OF 3,5-DIAMINO-6-(2,3-DICHLOROPHENYL)-1,2,4-TRIAZINE

BACKGROUND OF THE INVENTION

1. Field of the Invention

This invention relates to an improved and economical process for the preparation of 3,5-diamino-6-(2,3-dichlorophenyl)-1,2,4-triazine, which is also known as lamotrigine. This is a new structural class of antiepileptic drug.

2. Description of the Prior Art

The need for a drug, which will be effective in the patients who do not satisfactorily respond to conventional antiepileptic drugs has always been there. Also, a selectivity of specific mechanism of action reduces the side effect burden as in the case with Lamotrigine i.e. 3,5-diamino-6-(2,3-dichlorophenyl)-1,2,4-triazine (I). Lamotrigine, the selective sodium channel blocker which inhibits synaptosomal excitatory neurotransmitter release, is a use and voltage dependent inhibitor of presynaptic sodium channels.

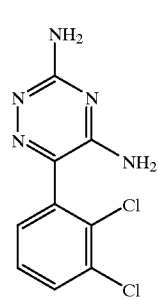

(I)

Lamotrigine can be prepared according to the literature procedure described in the U.S. Pat. No. 4,602,017 which comprises reacting 2,3-dichloro acyl chloride with cuprous cyanide and potassium iodide in dry xylene medium and reacting the resultant dichloro acyl cyanide with aminoguanidine bicarbonate and cyclizing the reaction product in presence of 10% methanolic KOH or n-propanol to produce lamotrigine.

In the U.S. Pat. No. 4,602,017, acid chloride (II) (1 mole equivalent) was converted to acyl cyanide (III) (Reaction-1) by using metal cyanide viz. copper cyanide (~2.4 mole equivalent) and potassium iodide (~2.4 mole equivalent) in dry xylene (~20 vol./wt of acid chloride) as solvent.

Reaction-1

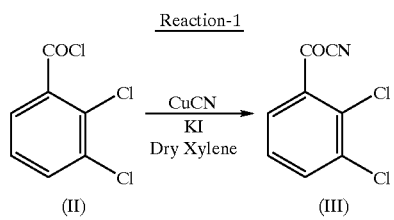

In the reaction of acid chloride (II) to acyl cyanide (III) as in the Reaction-1, the voluminous quantities of solvent dry xylene, demands the larger reactor size for comparatively smaller quantities of acid chloride.

Also, the use of potassium iodide increases the cost of the process. In the final step of cyclization, an alcoholic solvent i.e. alcoholic KOH further adds up to the cost.

The activation of copper cyanide by using metal iodide is certainly noteworthy.

However, taking into view the cost of metal iodide viz. potassium iodide, the subject invention looks into the possibility of avoiding the use of it, to reduce the manufacturing cost. Moreover, use of the solvent viz.dry xylene, in such a large quantities adds to the cost of the product.

SUMMARY OF THE INVENTION

The object of the present invention is to provide a process for the preparation of lamotrigine which is cost effective.

Another object of the present invention is to provide a process for the preparation of lamotrigine which does not use potassium iodide, or alocoholic potassium hydroxide and requiring lesser amount of solvent like toluene or xylene which are used only as a cosolvent.

Yet another object of the invention is to provide a process for production of lamotrigine of high grade purity, highly satisfactory impurity profile, white in color, free flowing, having lower moisture content, which can be efficiently and effectively dried and can be easily converted into pharmaceutical compositions.

Accordingly the present invention provides an improved process for the preparation of 3,5-diamino-6-(2,3-dichlorophenyl)-1,2,4-triazine of formula I, which process comprising the steps of:

(a) reacting 2,3-dichlorobenzoyl-chloride (II) with cuprous cyanide in presence of acetonitrile and a cosolvent, to produce dichlorobenzoyl cyanide (III);

Reaction-2

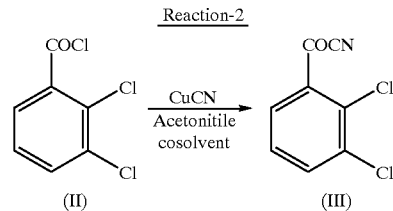

(b) reacting dichlorobenzoyl cyanide (III) obtained in step (a) with aminoguanidine bicarbonate to produce the intermediate product of formula (IV), and

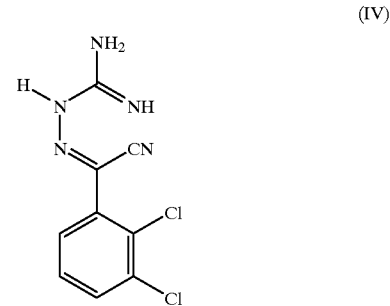

(IV)

(c) cyclizing said intermediate of formula IV in presence of aqueous potassium hydroxide to produce 3,5-diamino-6-(2,3-dichlorophenyl)-1,2,4-triazine.

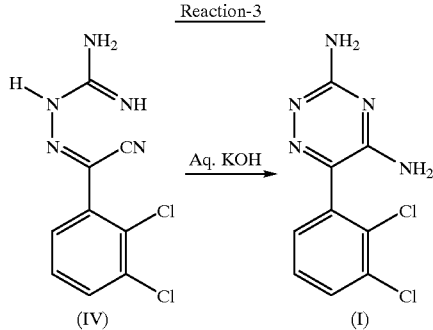

Reaction-3

DETAILED DESCRIPTION OF THE INVENTION

The present invention targeted towards lowering the cost of Lamotrigine provides an industrially economical process for the preparation of Lamotrigine i.e. 3,5-diamino-6-(2,3-dichlorophenyl)-1,2,4-triazine (I).

In the instant invention, 2,3-dichlorobenzoylchloride (II) is transformed into 2,3-dichlorobenzoyl cyanide (III), which is the building block for the heterocyclic ring, as shown in Reaction-2 above. Acetonitrile is used for complexation with copper cyanide. Copper cyanide complexed with acetonitrile as solvent gives good yields. Also, acetonitrile forms the part of solvent system, e.g. acetonitrile: toluene or acetonitrile: xylene. Thus, use of excessive dry xylene has been replaced by mixture of acetonile and toluene/xylene in the ratio ranging from 1:6 to 1:3 and more preferably 1.2:6. Use of toluene helps to increase the reaction temperature. Also the use of potassium iodide is omitted. Due to this modification the demand on the reactor size is also lower. In another aspect cyclization of the intermediate (IV) (obtained by reacting acyl cyanide (III) with aminoguanidine bicarbonate) to form the heteroaromatic ring system of lamotrigine, can be carried out by using 0.5% to 1.5% aqueous KOH preferably 0.95% to 1.05% of aqueous KOH (as shown in reaction-3) instead of 10% methanolic KOH or only n-propanol, which are costly.

While the reaction of step (b) is carried out at room temperature, the preferred temperature range for reaction of step (a) is 40° C. to reflux temperature and that of cyclization of step (c) is 80° C. to reflux temperature.

With the help of this route of reaction, the yield of lamotrigine improves by around 5%.

In order to obtain lamotrigine of high grade purity, highly satisfactory impurity profile, white in color, free flowing, having lower moisture content, which can be efficiently and effectively dried and can be easily converted into pharmaceutical compositions, charcoalization in alcohol such as methanol was carried out.

PREPARATORY EXAMPLES

The invention is explained in detail in the following examples which are provided by way of illustrations only and should therefore not be construed to limit the scope of the invention.

Example 1

In a mixture of 128 gm. of copper cyanide, 120 ml. of acetonitrile and 200 ml. of toluene, the solution of 200 gm. of 2,3-dichlorobenzoylchloride (II) in 250 ml of toluene was added. The reaction mixture was refluxed for 16 hour. After filtration, the solvent was removed under reduced pressure to give 200 ml of oily 2,3-dichlorobenzoyl cyanide (III).

Example 2

In the solution of 2.28 Kg. of sulphuric acid and 1.20 lit. of water was added 260 gm. aminoguanidinebicarbonate. To it added 2,3-dichlorobenzoyl cyanide i.e. compound-III (from Example-1) in 800 ml. of acetonitrile and stirred for 60 hrs. Filtered the solid. The solid was father added to aqueous NaOH. The mixture was stirred for 1 hr. at pH 11–12. The material obtained after filtration i.e. compound-IV was used in Example-3.

Example 3

Compound (IV), obtained from 2,3-dichlorobenzoyl cyanide (III) was refluxed in 1.5 lit. of 1% KOH solution for 1.5 hr to give white solid. It was filtered and washed with water to give 107 gm. of Lamotrigine.

m.p.: 216–218° C.

IR(KBr):3450, 3315, 1646, 1619, 1557, 1490, 792 cm$^{-1}$ $^1$H NMR(DMSO, 400 MHz)δ: 7.61(d,1H,J=1.5 Hz),7.35(t, 1H,J=7.9 Hz), 7.26(d×d, 1H,J$_1$=1.6 Hz,J$_2$=7.6 Hz)

Mass: 256.4(10%)

I claim:

1. An improved process for the preparation of 3,5-diamino-6-(2,3-dichlorophenyl)-1,2,4-triazine of formula (I)

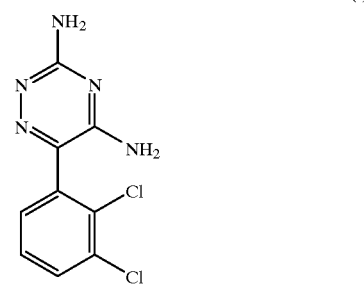

which process comprises the step of:

(a) reacting 2,3-dichlorobenzoylchloride of formula (II) with cuprous cyanide in presence of acetonitrile and a cosolvent to produce dichlorobenzoyl cyanide (III)

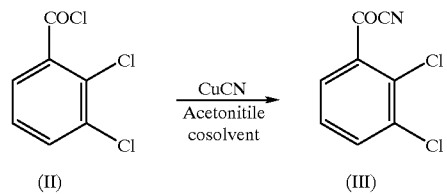

(b) reacting said dichlorobenzoyl cyanide (III) obtained in step (a) with aminoguanidine bicarbonate to produce the intermediate product of formula (IV)

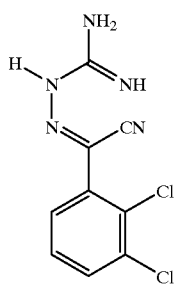

(c) cyclizing said intermediate of formula (IV) in presence of aqueous potassium hydroxide to produce 3,5-diamino-6-(2,3-dichlorophenyl)-1,2,4-triazine

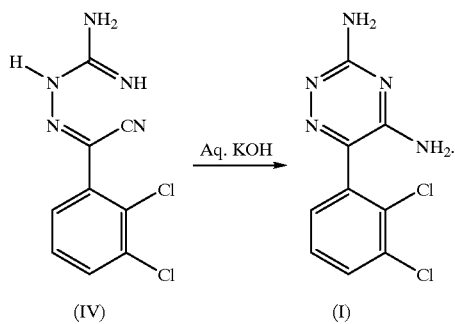

2. The process as claimed in claim 1 wherein said reaction of step (a) is carried out at a temperature ranging from 40° C. to reflux temperature, said reaction of step (b) is carried out at room temperature, and said cyclization of step (c) is carried out at a temperature ranging from 80° C. to reflux temperature.

3. A process as claimed in claim 1, wherein said cosolvent used in step (a) is toluene.

4. A process as claimed in claim 1 wherein said cosolvent used in step (a) is xylene.

5. A process as claimed in claim 1, wherein the range of ratio of volumes of acetonitrile to cosolvent in step (a) is 1:6 to 1:3.

6. A process as claimed in claim 5, wherein said ratio of volumes of acetonitrile to cosolvent is 1.2:6.

7. A process as claimed in claim 1, wherein 0.95% to 1.05% aqueous KOH is used in cyclization.

8. The process as claimed in claim 1 wherein the product obtained by step (c) is further charcoalized in alcohol to obtain a high purity grade, free flowing white product with highly satisfactory impurity profile and low moisture content, which can be efficiently and effectively dried and can be easily converted into pharmaceutical compositions.

9. The process as claimed in claim 8 wherein the alcohol used for charcoalization is methanol.

10. A process as claimed in claim 3, wherein the range of ratio of volumes of acetonitrile to cosolvent in step (a) is 1:6 to 1:3.

11. A process as claimed in claim 4, wherein the range of ratio of volumes of acetonitrile to cosolvent in step (a) is 1:6 to 1:3.

* * * * *